United States Patent [19]
Kragten et al.

[11] Patent Number: 5,959,153
[45] Date of Patent: Sep. 28, 1999

[54] PROCESS FOR DECOMPOSING CYCLOALKYLHYDROPEROXIDE

[75] Inventors: Ubaldus F. Kragten, Beek; Henricus A. C. Baur, Roermond, both of Netherlands

[73] Assignee: DSM N.V., Heerlen, Netherlands

[21] Appl. No.: 09/038,277

[22] Filed: Mar. 11, 1998

[30] Foreign Application Priority Data

Mar. 12, 1997 [BE] Belgium ................ 09700217

[51] Int. Cl.$^6$ .................................. C07C 45/00
[52] U.S. Cl. ................... 568/342; 568/832; 568/835; 568/833
[58] Field of Search .................. 568/376, 869, 568/835, 342, 570, 357, 361, 833, 832

[56] References Cited

U.S. PATENT DOCUMENTS

| | | |
|---|---|---|
| 2,675,407 | 4/1954 | Gallo . |
| 4,160,000 | 7/1979 | Hutto . |
| 4,328,372 | 5/1982 | Wu . |
| 5,175,316 | 12/1992 | Agar . |
| 5,206,441 | 4/1993 | Reimer ................. 568/342 |

FOREIGN PATENT DOCUMENTS

| | | |
|---|---|---|
| 0 004 105 | 9/1979 | European Pat. Off. . |
| 0 092 867 | 11/1983 | European Pat. Off. . |
| 0 659 726 | 6/1995 | European Pat. Off. . |
| 0 768 292 | 4/1997 | European Pat. Off. . |
| 178370 | 4/1965 | U.S.S.R. . |
| 1 382 849 | 2/1975 | United Kingdom . |

OTHER PUBLICATIONS

CA:87:5152 abs of nouv J Chim 1(1) pp. 13–14 by Formanek, 1977.

*Primary Examiner*—Gary Geist
*Assistant Examiner*—Jean F Vollano
*Attorney, Agent, or Firm*—Pillsbury Madison & Sutro Intellectual Property Group

[57] ABSTRACT

Process for decomposing a mixture containing cycloalkylhydroperoxide, which mixture includes an organic phase and an aqueous phase wherein, during the decomposition, at least one compound is present which meets the following parameters:

$$A > -0.5 \text{ and } B > -1.0 \quad (1)$$

A and B being dependent on $T_b$, $\rho$, $n_d$, $\epsilon_r$, $\delta_d$, $\delta_p$, $\delta_h$, $\delta$, $\mu$ and $E_{T(30)}$, where $T_b$ is the normal boiling point (° C.), $\rho$ is the density measured at 25° C. (kg/m$^3$), $n_d$ is the refractive index (–), $\epsilon_r$ is the relative dielectric constant (–), $\delta_d$ is the Hansen solubility parameter for a dispersion (MPa$^{1/2}$), $\delta_p$ is the Hansen solubility parameter for polarity (MPa$^{1/2}$), $\delta_h$ is the Hansen solubility parameter for hydrogen bridges (MPa$^{1/2}$), $\delta$ is the Scatchard-Hildebrant solubility parameter (MPa$^{1/2}$), $\mu$ is the dipole moment (Debey), and $E_{T(30)}$ is the Lewis donor/acceptor property (kcal/mol).

12 Claims, No Drawings

5,959,153

PROCESS FOR DECOMPOSING CYCLOALKYLHYDROPEROXIDE

BACKGROUND OF THE INVENTION

1. Field of the Invention

The invention relates to a process for decomposing a mixture containing cycloalkylhydroperoxide, which mixture comprises an organic phase and an aqueous phase.

2. Description of the Related Art

Such a process is already known from EP-A-4105, which describes that the decomposition of cycloalkylhydroperoxide is carried out in particular in the presence of sodium hydroxide. The cycloalkanones and cycloalkanols produced can be used in the preparation of caprolactam, which is in turn a raw material in the preparation of nylons. A drawback of the process described in EP-A-4105 is, however, that a continuous waste stream is formed, containing all kinds of mineral salts. This waste stream must either be reprocessed or it must be burned or be processed further. It is very important to have as few waste streams as possible in view of processing or reprocessing costs as well as environmental considerations.

BRIEF SUMMARY OF THE INVENTION

The reaction rate constant, a measure of the reaction rate, is an important parameter. The higher this constant, the more efficient the decomposition reaction. This means that the reaction can be carried out in a smaller reactor, which means a smaller investment, or, in the case of an existing reactor, that more decomposition products, in this case cycloalkanones and cycloalkanols, can be formed.

The purpose of the invention is to provide a process that produces as few waste streams as possible, without affecting the degree of conversion, selectivity and reaction rates in the decomposition of cycloalkylhydroperoxide into the desired products (alkanol/alkanone).

DETAILED DESCRIPTION OF THE INVENTION

This purpose is achieved by providing, during the decomposition, at least one compound which meets the following parameters:

$$A > -0.5 \text{ and } B > -1.0 \quad (1)$$

where A and B are functions having the following properties:

$$
\begin{aligned}
A = \ & 0.2307 * (T_b - 138.535)/62.36 + \\
& 0.2412 * (\rho - 935.639)/184.82 + \\
& 0.0554 * (n_d - 1.43695)/0.0635 + \\
& 0.3916 * (\epsilon_r - 15.0191)/18.6591 + \\
& 0.1208 * (\delta_d - 16.6807)/1.738 + \\
& 0.4135 * (\delta_p - 6.11284)/5.1640 + \\
& 0.3462 * (\delta_h - 8.04954)/6.9713 + \\
& 0.4177 * (\delta - 20.6908)/5.08667 + \\
& 0.3370 * (\mu - 1.73197)/1.20018 + \\
& 0.3723 * (E_{T(30)} - 41.14)/7.61433
\end{aligned} \quad (2)
$$

$$
\begin{aligned}
B = \ & -0.3009 * (T_b - 138.535)/62.36 - \\
& 0.3882 * (\rho - 935.639)/184.82 - \\
& 0.5914 * (n_d - 1.43695)/0.0635 + \\
& 0.1225 * (\epsilon_r - 15.0191)/18.6591 - \\
& 0.5506 * (\delta_d - 16.6807)/1.738 + \\
& 0.0970 * (\delta_p - 6.11284)/5.1640 + \\
& 0.2291 * (\delta_h - 8.04954)/6.9713 + \\
& 0.0583 * (\delta - 20.6908)/5.08667 +
\end{aligned} \quad (3)
$$

$$
\begin{aligned}
& 0.0381 * (\mu - 1.73197)/1.20018 + \\
& 0.1550 * (E_{T(30)} - 41.14)/7.61433
\end{aligned}
$$

where $T_b$ is the normal boiling point (° C.), $\rho$ is the density measured at 25° C. (kg/m$^3$), $n_d$ is the refractive index (–), $\epsilon_r$ is the relative dielectric constant (–) $\delta_d$ is the Hansen solubility parameter for a dispersion (MPa$^{1/2}$), $\delta_p$ is the Hansen solubility parameter for polarity (MPa$^{1/2}$), $\delta_h$ is the Hansen solubility parameter for hydrogen bridges (MPa$^{1/2}$), $\delta$ is the Scatchard-Hildebrant solubility parameter (MPa$^{1/2}$), $\mu$ is the dipole moment (Debey) and $E_{T(30)}$ is the Lewis donor/acceptor property (kcal/mol).

The values of the aforementioned properties can be found in the following references: "Properties of Liquids and Gases", fourth edition, Reid, Prausknitz & Poling, McGraw Hill, 1987; "Properties of Polymers (Their Correlation with Chemical Structure)", D. W. van Krevelen, Elsevier Scientific Publishing Company, Amsterdam 1990, "Solvents and Solvent Effects in Organic Chemistry", Ch. Reichardt, VCH Verlagsgesellschaft mbH, Weinheim (Germany, FRG, 1990) and "DIPR—Tables, Physical and Thermodynamic Properties of Pure Components", Daubert & Danner, Taylor & Francis, 1994.

Examples of such compounds are alcohols with 1–6 C atoms, aldehydes with 1–6 C atoms and organic sulphoxides having the general formula R$^1$SOR$^2$, in which R$^1$ and R$^2$ represent alkyl groups with 1–6 C atoms or aryl groups. Examples of such compounds are methanol, ethanol, 1-propanol, glycerol, dimethyl sulphoxide (DMSO), sulfolane, dimethyl sulfone, propyl sulfone, butyl sulfone, phenylsulfone, butyl sulfoxide, phenylsulfoxide, diethylene glycol, ethylene glycol, methanal (formaldehyde), ethanal (acetaldehyde) and propanal (propionaldehyde). Preferably use is made of alcohols and/or aldehydes with 1–4 C atoms. In particular, use is made of methanol, ethanol and/or 1-propanol.

These compounds may optionally be diluted with water.

The amount of this compound or these compounds is at least 1 wt. %, relative to the total reaction mixture. The maximum amount is 50 wt. %, relative to the total reaction mixture. If more than 50 wt. % is used, the reaction rate will not increase any further and this is therefore economically not advantageous. Preferably 10–30 wt. % is used, in particular 12–20 wt. % is preferred.

In addition to these compounds, the aqueous phase may also contain alkali metal compounds, preferably alkali metal compounds that are soluble in water. Alkali metal hydroxides, alkali metal carbonates and alkali metal carboxylates may be used. Preferably alkali metal compounds of mono- and dicarboxylic acids are used, more preferably, carboxylic acids containing 1–24 C atoms, and still more preferably 1–12 C atoms are used. Sodium and potassium are preferred for use as the alkali metal. Preferably the alkali metal is sodium. Examples of carboxylic acids are acetic acid, propionic acid, butyric acid, adipic acid, hexanoic acid, pentanoic acid, propane dicarboxylic acid, hexane dicarboxylic acid, stearic acid and decanoic acid. Preferably sodium hydroxide and/or sodium carbonate are used as the alkali metal compounds. Mixtures of different alkali metal compounds may also be used.

If alkali metal compounds are used, then the amount used is at most 35 wt. %, based on the aqueous phase present in addition to the organic phase containing cycloalkylhydroperoxide. It is also possible to use a higher concentration of alkali metal compounds, for example 45 wt. %. The drawback of a higher salt concentration, however, is that crystallization of metal carboxylates, for example, may take place when the process stream cools. Crystallization can be prevented by diluting the process stream.

By replacing all or part of the amount of alkali metal compound by a compound that satisfies the above parameters (1)–(3), a considerable saving in costs can be realized as, for example, the alcohol can be recycled in a far more efficient and economical manner than the alkali metal compound.

It has been found that both very good reaction rates and very good selectivity towards the desired reaction products (alkanol/alkanone) are obtained in particular if sodium hydroxide is used as the alkali metal compound and 1-propanol or ethanol as the alcohol. The combination of sodium carbonate and methanol also yields good results.

The mixture containing cycloalkylhydroperoxide can be obtained through oxidation of a cycloalkane with 5–12 C atoms in the ring in the liquid phase with a gas containing oxygen. The cycloalkane is preferably cyclopentane, cyclooctane, cyclododecane or, in particular, cyclohexane. In addition to the cycloalkylhydroperoxide, the oxidation mixture obtained may also contain other peroxides, for example dicycloalkylperoxide. For convenience, the term 'cycloalkylhydroperoxides' is understood to include all such peroxides.

A compound satisfying above parameters is different from the cycloalkane to be oxidized and the cycloalkane oxidation products.

The oxidation takes place in the liquid phase. The gas containing oxygen can be, for example, atmospheric air or pure oxygen. Suitable oxidation temperatures are between 120° C. and 200° C. Preferably a temperature of between 140° C. and 190° C. is used.

The reaction is carried out for 5 min.–24 hours. The pressure must be such that a liquid phase is sustained in the system. The pressure will usually be between 0.3 MPa and 5 MPa, preferably between 0.4 MPa and 2.5 MPa.

The oxidation is preferably carried out in continuous mode, preferably in a system of reactors connected in series, a compartmentalized reactor system or a tube reactor. If temperature control is to take place during the reaction, this generally takes place by discharging the heat of reaction via a gas stream, via intermediate cooling or via other methods known to a person skilled in the art. Preferably reactors with an inert interior are chosen, to prevent the risk of the introduction of transition elements (which promote the decomposition of cycloalkylhydroperoxide) into the mixture to be oxidized. It will be clear that if a negligible amount of metal ions are introduced into the oxidation mixture, this will have no substantial influence on the reaction and, in the context of the present invention, an uncatalyzed cycloalkane oxidation is said to take place. Unlike the uncatalyzed cycloalkane oxidation, the catalyzed oxidation, which usually involves the addition of a metal such as cobalt and chromium, results in a reaction mixture containing a relatively small amount of cycloalkylhydroperoxide relative to cycloalkanone+cycloalkanol. In spite of that, the process according to the invention is also advantageous where a relatively small amount of cycloalkylhydroperoxide is present.

The product formed in the uncatalyzed oxidation of for example cyclohexane generally includes at least an amount of cyclohexylhydroperoxide in wt. % comparable to the amount of cyclohexanol+cyclohexanone. Often the mixture obtained after the uncatalyzed reaction contains more than twice as much cyclohexylhydroperoxide as cyclohexanol+cyclohexanone. In contrast, the catalyzed oxidation results in a mixture that contains less than 50% cyclohexylhydroperoxide relative to the wt. % cyclohexanol+cyclohexanone. Often there is even less than 40% peroxide relative to the wt. % cyclohexanol+cyclohexanone.

The concentration of cycloalkylhydroperoxide in the reaction mixture leaving the (last) oxidation reactor is generally between 0.1 wt. % and 8.0 wt. %. The concentration of cycloalkanone in this mixture is generally between 0.1 wt. % and 10 wt. %. The concentration of cycloalkanol in this mixture is generally between 0.1 wt. % and 15 wt. %. The degree of cycloalkane conversion relative to this reaction mixture is generally between 0.5 wt. % and 25 wt. %. The degree of cycloalkane conversion is preferably between 2 wt. % and 10 wt. %.

The decomposition reaction is preferably carried out in the presence of at least one metal salt that promotes decomposition. This is generally a salt of a transition element. Examples of suitable transition elements are cobalt, chromium, manganese, iron, nickel, copper or mixtures hereof, such as a mixture of cobalt and chromium. The metal salt is preferably soluble in water. Metal sulfates and metal acetates have proven to be very useful salts. The amount of metal salt may be 0.1–1000 ppm, calculated as metal, relative to the weight of the aqueous phase. It is however also possible to use greater amounts of metal salt. Preferably 0.1–10,ppm metal is used. The metal salt can be added to the mixture containing cycloalkyl as an aqueous solution, optionally in combination with the alkali metal compound. It is also possible to add the metal to the reaction mixture as an organic salt, dissolved in an organic solvent. The cycloalkane corresponding to the cycloalkylhydroperoxide can then, for example, be used as the solvent. It is also possible to apply the metal salt to a carrier.

The decomposition reaction takes place by causing the mixture to react for 5–300 min. The residence time in the decomposition reactor is preferably 15–120 min., but a person skilled in the art will easily be able to determine the required time.

The decomposition reaction preferably takes place in a fixed-bed reactor as a relatively high catalyst concentration is obtained. This is particularly advantageous if use is made of cycloalkylhydroperoxide mixtures with relatively low concentrations.

To ensure an efficient cycloalkylhydroperoxide decomposition, the volume ratio of the aqueous phase and the organic phase in the decomposition reactor is preferably higher than 0.02. Preferably a ratio of 0.05–0.25 is used. These volume ratios are, however, not critical, and may optionally be adjusted by a person skilled in the art.

The cycloalkylhydroperoxide decomposition may take place at a temperature of between 20° C. and 180° C. Preferably the decomposition takes place at a temperature of between 60° C. and 100° C.

The decomposition reaction may be carried out both at atmospheric pressure and at elevated pressure. The decomposition reaction is advantageously carried out at a pressure of the same order of magnitude as the oxidation pressure used in the process; it may however also be advantageous to evaporate part of the cycloalkane after the oxidation by reducing the pressure, causing flashing. The pressure during the decomposition reaction is then preferably 0.1–0.6 MPa; more preferably the decomposition reaction is carried out at atmospheric pressure.

After the decomposition, the aqueous phase may be separated from the organic phase. The organic phase may subsequently be washed to remove any remaining aqueous phase containing residual salt still present. The aqueous phase can be reused in the decomposition reaction. The aqueous phase then already contains alkali metal salts of carboxylic acids. The carboxylic acids may be formed as a by-product in the oxidation or in the decomposition, in which case a salt of the carboxylic acid will be formed owing to the presence of the alkali metal. Reuse presents the advantage that the water phase/organic phase ratio can be simply set and controlled.

If sodium carbonate is used as the alkali metal compound, salts of carboxylic acids are formed in the decomposition. These salts are removed from the aqueous phase and are subsequently burned, as a result of which sodium carbonate is again formed. This sodium carbonate can subsequently be used in the decomposition.

Alcohols that are used as a compound according to parameters (1)–(3) can be simply removed from the reaction mixture, for example by distillation, and can be used again. Techniques other than distillation may also be used for removing the alcohols; an example of such a technique is separation using membrane units.

Distillation of the organic phase ultimately results in a mixture of cycloalkanone and cycloalkanol.

The decomposition reaction can be carried out both in continuous mode and batchwise.

Comparative Experiment A

At a temperature of 66° C., 30 ml of a basic aqueous phase in which NaOH (1000 mmol NaOH/kg) is dissolved together with 2 g of an aqueous $COSO_4$ (95 ppm Co) solution were added to 250 ml of a cyclohexane oxidation mixture containing 190 mmol cyclohexylhydroperoxide (CHHP), 40 mmol cyclohexanone (ONE) and 90 mmol cyclohexanol (OL) per kilogram. The decomposition that took place was followed using iodometric titration. The first-order rate constant was 0.016 min$^{-1}$. The selectivity towards OL+ONE was 87.5%. The OL/ONE ratio was 0.50.

EXAMPLE I

Comparative Experiment A was repeated, except that 7.5 g of the basic aqueous phase was replaced by 7.5 g of 1-propanol. The reaction temperature was 66° C. The first-order rate constant was 0.015 min$^{-1}$. The selectivity towards OL+ONE was 93.6%. The OL/ONE ratio was 0.55. Separation of the organic and aqueous phases and distillative removal of the 1-propanol from the aqueous phase resulted in an aqueous phase that was decreased by 27% compared with the aqueous phase of Comparative Experiment A. The aqueous phase is the waste stream containing the mineral salts.

EXAMPLE II

Comparative Experiment A was repeated, except that 7.5 g of the basic aqueous phase was replaced by 7.5 g of methanol. The reaction temperature was 66° C. The first-order rate constant was 0.013 min$^{-1}$. Again the aqueous phase remaining after the removal of the methanol was decreased more than proportionally.

EXAMPLE III

Comparative Experiment A was repeated, except that 7.5 g of the basic aqueous phase was replaced by 7.5 g of ethanol. The reaction temperature was 66° C. The first-order rate constant was 0.020 min$^{-1}$.

EXAMPLE IV

Comparative Experiment A was repeated, except that 7.5 g of the basic aqueous phase was replaced by 3.75 g of methanol and 3.75 g of 1-propanol. The reaction temperature was 66° C. The first-order rate constant was 0.014 min$^{-1}$.

Comparative Experiment B

Comparative Experiment A was repeated, except that $Na_2CO_3$ (1000 mmol $Na_2CO_3$/kg) was used instead of NaOH. The reaction temperature was 66° C. The first-order rate constant was 0.00094 min$^{-1}$. The selectivity towards OL+ONE was 90.3%. The OL/ONE ratio was 0.60.

EXAMPLE V

Comparative Experiment B was repeated, except that 7.5 g of the $Na_2CO_3$ solution was replaced by 7.5 g of methanol. The reaction temperature was 66° C. The first-order rate constant was 0.010 min$^{-1}$. The selectivity towards OL+ONE was 92.5%. The OL/ONE ratio was 0.65. The reaction rate constant was significantly improved and the aqueous phase had decreased by 26.5%.

Comparative Experiment C

Comparative Experiment B was repeated, except that 3 g of a Co catalyst on $TiO_2$ (2.6% Co) instead of 2 g of the $CoSO_4$ solution was added to the aqueous phase. The reaction temperature was 66° C. The first-order rate constant was 0.005 min$^{-1}$. The selectivity towards OL+ONE was 103.3%. The OL/ONE ratio was 0.74.

EXAMPLE VI

Comparative Experiment C was repeated, except that 25 g of methanol was added to the aqueous phase. The reaction temperature was 62° C. The first-order rate constant was 0.017 mine. The selectivity towards OL+ONE was 104%. The OL/ONE ratio was 0.74. After separation of the organic phase and the aqueous phase, the methanol was removed from the aqueous phase by distillation. The resulting aqueous phase had a smaller volume than the resulting aqueous phase in Comparative Experiment C. The reaction rate constant was moreover substantially higher.

Comparative Experiment D

Comparative Experiment A was repeated, except that a mixture of NaOH (500 mmol/kg) and $Na_2CO_3$ (500 mmol/kg) was added to the reactor instead of the NaOH. The reaction temperature was 66° C. The first-order rate constant was 0.019 min$^{-1}$.

EXAMPLE VII

Comparative Experiment D was repeated, except that 7.5 g of the basic aqueous phase was replaced by 7.5 g of methanol. The reaction temperature was 66° C. The first-order rate constant was 0.030 min$^{-1}$.

Comparative Experiment E

Comparative Experiment D was repeated, except that 3 g of a Co catalyst on $TiO_2$ (2.6% Co) was added to the aqueous phase instead of the $CoSO_4$ solution. The reaction temperature was 66° C. The first-order rate constant was 0.009 min$^{-1}$.

EXAMPLE VIII

Comparative Experiment E was repeated, except that 7.5 g of the basic phase was replaced by 7.5 g of methanol. The reaction temperature was 66° C. The first-order rate constant was 0.030 min$^{-1}$. Comparison of Comparative Experiment E and Example VIII shows a good improvement in the reaction rate constant as a result of the addition of methanol.

Comparative Experiment F

At a temperature of 56° C., 1.6 g of catalyst consisting of Co on TiO$_2$ (1.3% Co) was combined with 250 ml of a cyclohexane oxidation mixture containing 190 mmol cyclohexylhydroperoxide (CHHP), 40 mmol cyclohexanone (ONE) and 90 mmol cyclohexanol (OL) per kilogram. The first-order rate constant was 0.0003 min$^{-1}$.

EXAMPLE IX

Comparative Experiment F was repeated, except that 30 g of methanol was added. The reaction temperature was 56° C. The first-order rate constant was 0.0009 min$^{-1}$.

Comparative Experiment G 17.0 Ml/min of a cyclohexane oxidation mixture containing 153 mmol CHHP, 53 mmol ONE and 105 mmol OL per kilogram was added to the first reactor. In addition, 1.95 ml/min of an aqueous phase was added, in which NaOH (750 mmol NaOH/kg), Na$_2$CO$_3$ (354 mmol/kg Na$_2$CO$_3$), COSO$_4$ (4.3 ppm Co) and a mixture of sodium salts of mono- and dicarboxylic acids (C$_1$ up to and including C$_6$) (20 wt. % in water) had been dissolved. The decomposition of the CHHP was carried out at a temperature of 62° C. in both reactors. The rate of decomposition was followed using iodometric titration. The first-order rate constant over both reactors was 0.08 min$^{-1}$. The degree of conversion after the second reactor was 89%.

EXAMPLE X

Comparative Experiment G was repeated, except that 1.47 ml/min of an aqueous phase was added in which NaOH (750 mmol NaOH/kg), Na$_2$CO$_3$ (354 mmol/kg Na$_2$CO$_3$), COSO$_4$ (4.3 ppm Co) and a mixture of sodium salts of mono- and dicarboxylic acids (C$_1$ up to and including C$_6$) (20 wt. % in water) had been dissolved. At the same time, 0.48 ml/min methanol was also added. The decomposition of the CHHP was carried out at a temperature of 62° C. in both reactors. The first-order rate constant over both reactors was 0.15 min$^{-1}$. The degree of conversion after the second reactor was more than 95%. In comparison with Comparative Experiment G, the aqueous phase, and hence the waste stream, had decreased by more than 25%.

What is claimed is:

1. A process comprising:
   introducing a mixture comprising;
   cycloalkylhydroperoxide,
   an aqueous phase, and
   an organic phase; and
   decomposing cycloallylhydroperoxide, in said mixture, to form an alkano and alkanone,
   wherein said decomposing is assisted by at least one compound including an alcohol with 1–6 C atoms, an aldehyde with 1–6 C atoms or an organic sulphoxide represented by the general formula R$^1$SOR$^2$, where R$^1$ and R$^2$ independently represent alkyl or aryl groups.

2. The process according to claim 1, wherein the compound is at least one member selected from the group consisting of alcohols with 1–4 C atoms and aldehydes with 1–4 C atoms.

3. The process according to claim 2, wherein the compound is at least one member selected from the group consisting of methanol, ethanol and 1-propanol.

4. The process according to any one of claims 2-3 and 1, wherein the compound is used in an amount of at least 1 wt. %, relative to the total mixture.

5. The process according to claim 4, wherein a maximum amount of the compound is 50 wt. %, relative to the total mixture.

6. The process of claim 1, wherein decomposing is in the presence of an ankali metal compound.

7. The process according to claim 6, wherein the alkali metal compound is a member selected from the group consisting of alkali metal hydroxides, alkali metal carbonates and alkali metal carboxylates.

8. The process according to claim 7, wherein the alkali metal compound is at least one member selected from the group consisting of sodium hydroxide and sodium carbonate.

9. The process according to claim 6, wherein the alkali metal compound is sodium hydroxilde and the at least one compound is 1-propanol.

10. The process according to claim 6, wherein the alkali metal compound is sodium carbonate and the at least one compound is methanol.

11. The process according to claim 1, wherein between 0.1 and 1000 ppm of a salt of a transition element that promotes decomposition is also present during the decomposing.

12. The process according to claim 1, further comprising obtaining the mixture containing cycloalkylhydroperoxide by oxidizing a corresponding cycloalkane at a temperature of between 120° C. and 200° C. and a pressure of between 0.3 MPa and 5 MPa, in the absence of an oxidation catalyst.

* * * * *